(12) United States Patent
Bang

(10) Patent No.: US 9,468,748 B2
(45) Date of Patent: Oct. 18, 2016

(54) MULTI-NEEDLE ASSEMBLY WITH READILY ADJUSTABLE STRUCTURE

(71) Applicant: PANACE CO., LTD., Seongnam-si (KR)

(72) Inventor: Si-Yeol Bang, Yongin-si (KR)

(73) Assignee: PANACE CO., LTD., Seongnam-Si, Gyeonggi-Do (KR)

( * ) Notice: Subject to any disclaimer, the term of this patent is extended or adjusted under 35 U.S.C. 154(b) by 120 days.

(21) Appl. No.: 14/401,626

(22) PCT Filed: May 23, 2013

(86) PCT No.: PCT/KR2013/004542
§ 371 (c)(1),
(2) Date: Nov. 17, 2014

(87) PCT Pub. No.: WO2013/180422
PCT Pub. Date: Dec. 5, 2013

(65) Prior Publication Data
US 2015/0133862 A1    May 14, 2015

(30) Foreign Application Priority Data
May 31, 2012   (KR) .................. 10-2012-0058212

(51) Int. Cl.
*A61M 5/00* (2006.01)
*A61M 37/00* (2006.01)
*A61B 17/20* (2006.01)
*A61B 17/00* (2006.01)

(52) U.S. Cl.
CPC ........ *A61M 37/0015* (2013.01); *A61B 17/205* (2013.01); *A61B 2017/00756* (2013.01); *A61B 2017/00761* (2013.01); *A61B 2017/00769* (2013.01); *A61M 2037/0023* (2013.01)

(58) Field of Classification Search
CPC ............... A61M 2037/0023; A61M 37/0015; A61M 5/46
USPC ....................................... 604/117
See application file for complete search history.

(56) References Cited

U.S. PATENT DOCUMENTS

2011/0276006 A1   11/2011   Matthias et al.
2012/0136300 A1   5/2012    Schoonmaker et al.

FOREIGN PATENT DOCUMENTS

| EP | 2457605 A2 | 5/2012 |
| JP | 2011-527203 A | 10/2011 |
| KR | 20-2009-0008677 U | 8/2009 |

(Continued)

Primary Examiner — Deanna K Hall
(74) Attorney, Agent, or Firm — Rabin & Berdo, P.C.

(57) ABSTRACT

A multi-needle assembly according to the present invention includes: a plurality of needles; a central hub for supporting the needles with the front part of the needles exposed and the rear part thereof fixedly surrounded; a suction cap with the front having needle penetration holes for receiving the needles, the suction cap surrounding the needles and in a sealed manner one side of the central hub; and an adjustment part rotatably connected to the rear end of the suction cap and screwed around one side of the central hub for moving the central hub forward or backward with regard to the suction cap by rotation so as to adjust the length of exposure of the needles, wherein the adjustment part has one side inscribed with continuous numbers or a scale around. Thus the exposed length of the needles may be easily adjusted and confirmed as being desired, so that easy treatment is possible without an additional means for confirming.

10 Claims, 5 Drawing Sheets

(56) References Cited

FOREIGN PATENT DOCUMENTS

| KR | 10-2010-0015018 A | 2/2010 |
|---|---|---|
| KR | 10-2012-0044612 A | 5/2012 |

MULTI-NEEDLE ASSEMBLY WITH READILY ADJUSTABLE STRUCTURE

BACKGROUND OF THE INVENTION

1. Field of the Invention

The present invention relates to a multi-needle assembly for cosmetic procedure and more particularly, to a multi-needle assembly which is accurately adjustable in the depth to which it is injected into a skin, by a simple adjustment.

2. Description of the Related Art

The treatment of punching a plurality of fine holes in skin and flowing medication thereinto (referred to as 'multihole therapy' herein) is used for a variety of purposes such as treatment of skin troubles including wrinkles, spots, blemishes, stretch marks, acne, freckles, pigmentation, etc., maintenance of hair health and prevention of hair loss, or obesity treatment.

The multihole therapy provides speedy treatment effect, by utilizing recovery force of damaged skin to induce generation of new skin, or introducing medication through the fine holes.

However, the multihole therapy has shortcoming such as pains that a client can suffer, because many times, the practitioner relies on his/her intuition in practicing procedure of repeatedly needling client's skin. Injection of inconstant amount of medication is another shortcoming, due to irregular depths to which the needles are penetrated.

Further, middle-aged patients may not have appropriate skin turgor (i.e., tension) during puncturing of massive fine holes in the skin for the multihole therapy discussed above, in which case holes are not pierced to the depths as desired. That is, in the process of piercing a plurality of holes during multihole therapy as explained above, skin can be moved, tools such as needles can be slid out of accurate desired position or moved while being penetrated in the skin, thereby causing pains to the patients.

Korean Un-examined Patent Publication No. 10-2010-0015018 discloses "suction adapter for use in needle", according to which a syringe needle consisting of a needle and a needle hub is connected, and an air suction is connected and used to impose suction onto skin area to be injected, which includes a first space accommodating the needle hub therein, a penetrating hole extended in the first space, and a second space with open upper surface, and an air suction connector connected in fluid communication with the second space and connected to the air suction, whereby the suction adaptor is fixed in tight contact with the site to be injected, and skin layer is risen to a direction of the syringe by the suctioning of the air suction, after which fluid is injected to a depth into the skin as desired.

Korean Un-examined Patent Publication No. 10-2010-0015018 discloses a suction adaptor for use in multineedles, according to which the suction adaptor for use in multi-needles take consideration of length of exposure of the needles by employing a means for adjusting a depth of exposed needles, in which, specifically, a substantial portion of a second space and a protruding portion have heights corresponding to a length of the needles excluding exposed portions of the needles.

However, in use of the suction adaptor in the form as disclosed in KR 10-2010-0015018, although the length of exposure is adjustable, it is not the concept of actual 'adjustment', considering that it is impossible to adjust the length of exposure using a single suction adaptor, but requires a plurality of suction adaptors with individually corresponding sizes as needed, and also requires corresponding suction adaptors be replaced as needed, thereby causing inconvenience.

Korean Un-examined Publication No. 10-2012-0044612, filed by the present applicant, discloses "module for skin procedure" which addresses the problems mentioned above, according to which the module for skin procedure includes a main body having a hollow interior extending through both ends, a reciprocating assembly mounted within the main body, while being screw engaged along a length direction of the main body to be rotated and reverse rotated and moved forward and backward, a needle assembly mounted in contact with the reciprocating assembly in a manner of allowing the reciprocating assembly to rotate, and having a plurality of needles which enter and exit through one end of the main body, and a guide suction assembly in which an end is in contact with the skin, ends of the needles enter and exit, one end of the main body is engaged in a manner of allowing rotation, and in fluid communication with the skin which is in close contact with the end through which air is sucked in.

According to KR 10-2012-0044612, with use of the reciprocating assembly in screw engagement within the main body which moves forward and backward according to rotation and reverse rotation, and the rotating assembly which moves the reciprocating assembly for reciprocating movement within the main body so that the reciprocating assembly is moved forward and backward in rotating motion, it is advantageously possible to adjust the depth of injection accurately and precisely, with a simple manipulation of causing the needles of the needle assembly to enter and exit. However, because the module requires a separate means (i.e., measuring means) to check the length of exposure of the adjusted needles, it can be inconvenient. In other words, compared to the convenience of adjustment process of the exposure of the needles, the process of measuring to determine if the length of exposure is adjusted as desired, is inconvenient. Considering the nature of the procedure, it is very important to ensure precise adjustment of the depth of the needle injection in the skin. Indeed, procedure itself is impossible, without accurate determination on the length of the exposure. Accordingly, a solution to the shortcomings mentioned above is urgently required.

Further, in use of the module for skin procedure as disclosed in KR 10-2012-0044612, the guide suction assembly and the needle assembly are rotatable relative to each other. Accordingly, particularly those who are not familiar with the assemblies can damage the needles, when the guide suction assembly and the reciprocating assembly are rotated together with reference to the needle assembly.

DETAILED DESCRIPTION OF THE INVENTION

Technical Object

The present invention has been made to overcome the problems of the prior art discussed above, and therefore, an embodiment of the present invention relates to allowing a practitioner to adjust a depth of injection into a skin with a simple manipulation but with accuracy, and confirm the adjusted depth, thus providing stable maneuvering which prevents damages to the needles.

Means to Solve the Object

In order to accomplish the above-mentioned objects, the present invention provides a multineedle assembly, which may include a plurality of needles, a central hub exposing front portions of the needles, while surrounding rear portions of the needles to fix the needles in place, a suction cap surrounding one side of the needles and the central hub, being in close contact with the central hub, and comprising needle penetrating holes through which the needles are passed, and an adjusting portion rotatably connected to a rear end of the suction cap, being screw engaged with an edge of one side of the central hub to move the central hub with respect to the suction cap according to a direction of rotation, to thereby adjust a length that the needles are exposed. Herein, the adjusting portion may have a series of numbers or scale formed on one side along the direction of rotation.

According to another embodiment of the present invention, a multineedle assembly is provided, which may include a plurality of needles, a central hub exposing front portions of the needles, while surrounding rear portions of the needles to fix the needles in place, a suction cap surrounding one side of the needles and the central hub, being in close contact with the central hub, and comprising needle penetrating holes through which the needles are passed, and an adjusting portion rotatably connected to a rear end of the suction cap, being screw engaged with an edge of one side of the central hub to move the central hub with respect to the suction cap according to a direction of rotation, to thereby adjust a length that the needles are exposed. An adjusting tubular portion may be provided, forming a rear portion of the central hub and being connected to the adjusting portion, and the adjusting tubular portion may have a series of numbers or scale on one side along the direction of length.

The suction cap may include a close contact hole on a front portion which is separated from the needle penetrating holes, and a suction device connecting hole on one side which is in fluid communication with the close contact hole.

The needles are not protruded forward the suction cap, when the central hub is in a rear-most position with respect to the suction cap.

Either one of an outer side of the central hub and an inner side of the suction cap may include a guide groove, while the other one of the inner side of the suction cap and the outer side of the central hub that does not have the guide groove may include a guide protrusion to be slid along the guide groove.

An adjusting tubular portion may be provided, which forms a rear portion of the central hub and which is connected to the adjusting portion, and the adjusting portion may be configured to surround the adjusting tubular portion.

The adjusting tubular portion may include a series of numbers or scale in a direction of length.

The adjusting tubular portion may have a cylindrical shape which is partially cut away to render a plane thereon so that a scale portion is formed thereon, and the series of numbers or the scale formed on the adjusting tubular portion may be positioned on the scale portion.

The adjusting portion may be in close contact with a rear end of the suction cap, and may have a larger diameter than the suction cap.

The central hub may include a connecting portion to which the needles are fixedly connected, an adjusting tubular portion whose rear end is connected to a syringe nozzle and an edge is connected to the adjusting portion, wherein the connecting portion may include first penetrating holes through which the respective needles are passed, first communicating holes formed on rear ends of the first penetrating holes with increasing diameter, and wherein the adjusting tubular portion may include second penetrating holes in fluid communication with the syringe nozzle, second communicating holes formed on front ends of the second penetrating holes, wherein the second communicating holes are in fluid communication with all of the needles.

Two or more insert protrusions are formed on either one of a rear end of the connecting portion and a front end of the adjusting tubular portion, while insert holes to fittingly receive the insert protrusions therein are formed on the other one which do not have the insert protrusions.

At least part of the first penetrating holes may have larger diameter than that of the needles, and the needles may be fixed as adhesive is filled in the first penetrating holes.

The central hub and the suction cap may have a polygonal cross section.

Effect of the Invention

In the multineedle assembly according to one embodiment of the present invention, the adjusting portion and the adjusting tubular portion are screw engaged with each other and are gradulated, which in turn facilitate adjustment of length of exposure of the needle, and determination as to whether the length of the exposed needle corresponds to the desired length, so that procedure is performed with convenience, without having to use a separate means for checking the same.

Further, when the central hub is in rear-most end with respect to the suction cap, the needle is not protruded to a front of the suction cap, and at such position, the front end of the suction cap is in alignment with the front end of the needle, so that the degree of rotation of the adjusting portion corresponds to the length of exposure of the needle. Accordingly, adjustment of length of exposure of the needle is further facilitated.

Further, because the adjusting portion is configured with a larger diameter with reference to the central hub partially or entirely, practitioner can easily grab the adjusting portion and rotate the central hub with reference to the suction cap.

Further, because the central hub and the suction cap are provided with a guide groove and a guide protrusion, the possibility that the suction cap is rotated circumferentially with reference to the central hub in accordance with forward and backward movement of the central hub with reference to the suction cap, is prevented. Accordingly, damages to needle are prevented.

Further, since the adjusting tubular portion is cylindrically configured, but provided with a granulated portion on a plane formed by partial cutaway, appropriate degree of frictional force is generated between the adjusting portion and the adjusting tubular portion, thereby allowing easy maneuvering.

BRIEF DESCRIPTION OF THE DRAWINGS

The above and/or other aspects and advantages of the present invention will become apparent and more readily appreciated from the following detailed description, taken in conjunction with the accompanying drawings of which.

BEST MODE

Mode for Carrying Out the Invention

The preferred embodiments of the present invention will be explained below with reference to accompanied drawings.

The description is provided to explain the invention in detail to enable those with common knowledge in the technological field where the present invention pertains to easily carry out the invention, and not to be construed as being limiting technical concept and scope of the invention.

Further, sizes or shapes of the elements may be illustrated on exaggerated scale, for the purpose of clarity and convenience of explanation. Terms that are specifically defined in consideration of the configuration and operation of the invention are subject to change depending on intention or practice of a practitioner, or an operator, and the definitions of these terms should be based on the content provided herein.

Figure 1:
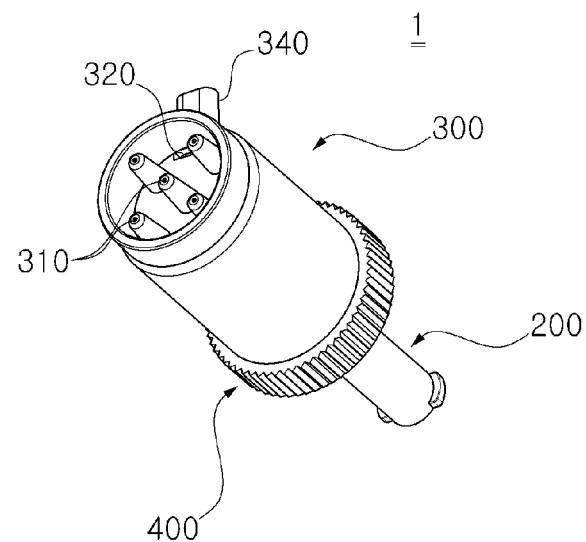
FIGS. 1 and 2 are perspective views of a multineedle assembly according to one embodiment of the present invention.
Figure 2:
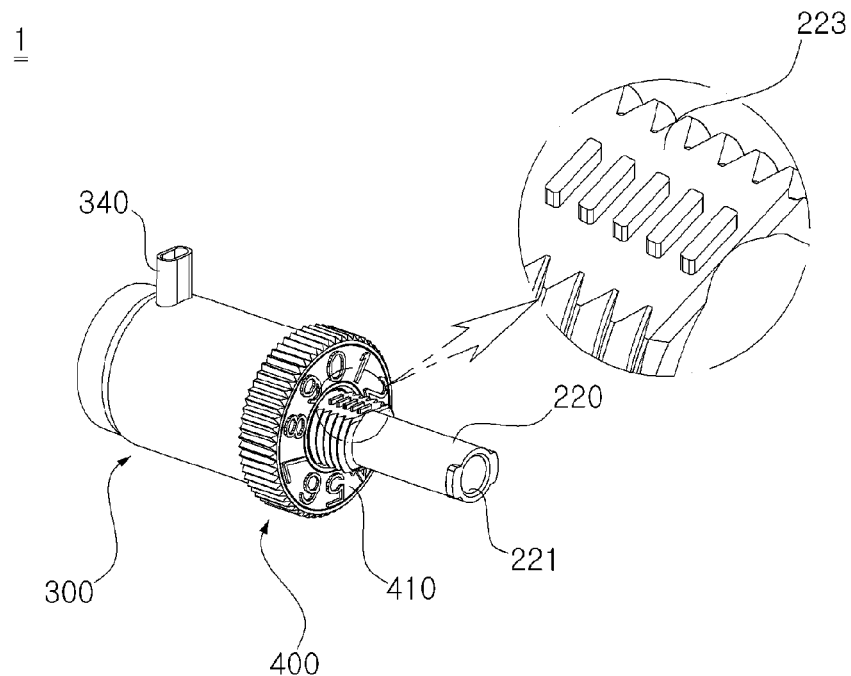
Figure 3:
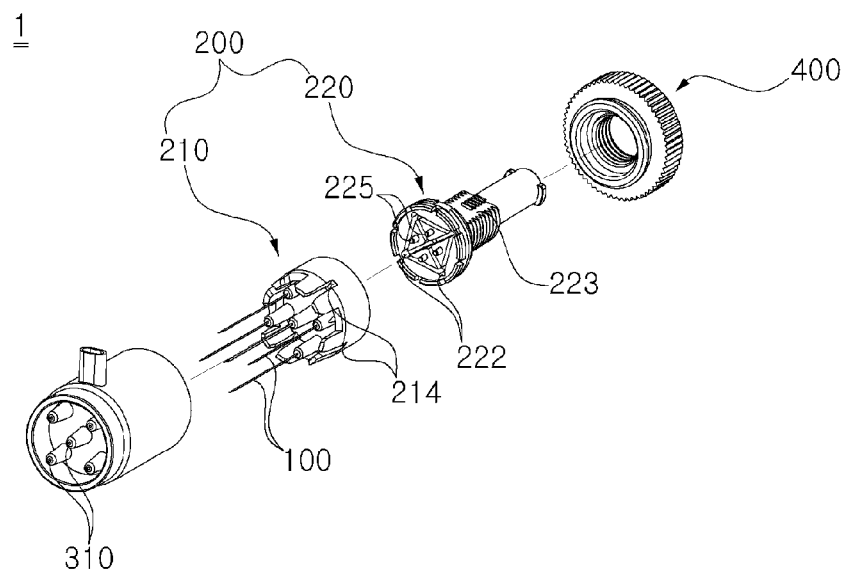
FIGS. 3 and 4 are exploded perspective views of the multineedle assembly of FIG. 1.
Figure 4:
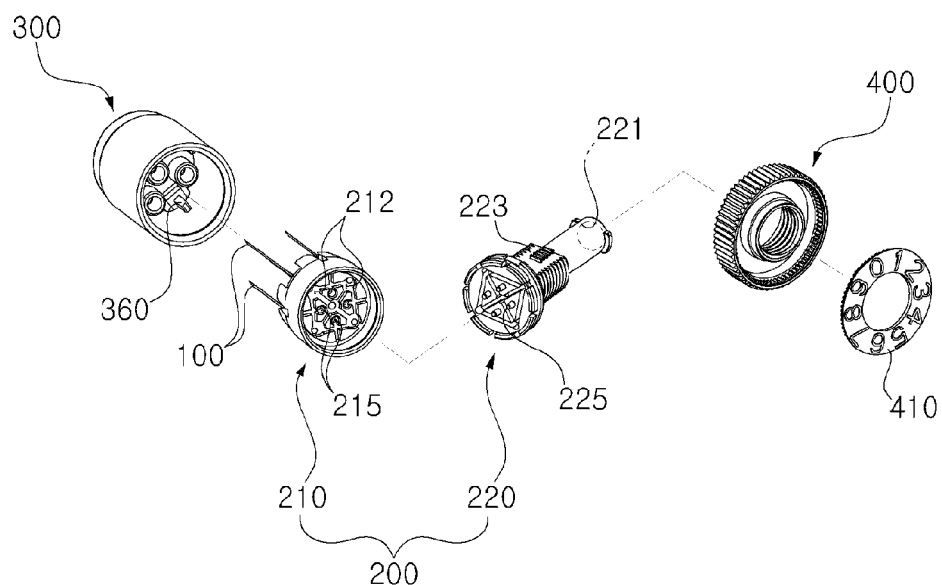

FIGS. 1 and 2 are perspective views of a multineedle assembly 1 according to one embodiment of the present invention, and FIGS. 3 and 4 are exploded perspective views of the multineedle assembly 1 of FIG. 1.

According to the present invention, the multineedle assembly 1 includes a plurality of needles 100, a central hub 200, a suction cap 300 and an adjusting portion 400. When in use, the multineedle assembly 1 according to the present invention is connected to a separate means such as a conventional syringe which is provided to inject fluid or the like. Particularly, the rear end of the central hub 200 is connected to a nozzle of the syringe. Herein, it is assumed that the direction where the suction cap 300 is formed is front, while the direction where syringe or the like is connected is rear.

The plurality of needles 100 are configured in a tubular form to allow fluid or medication introduced from the syringe to pass therethrough, and desirably formed from metal.

The central hub 200 serves as a center of the multineedle assembly 1 according to the present invention, and fixes the needles 100 in place.

The central hub 200 is mainly divided into a connecting portion 210 and an adjusting tubular portion 220, and as a whole, is connected to the rear end of the needle 100. That is, the central hub 200 is configured so as to expose the front portion of the needles 100, while fixedly surrounding the rear portions of the needles 100 so that the needles 100 are fixed in place. The manner in which the central hub 200 and the needles 100 are connected, is illustrated in FIG. 3. The central hub 200 will be additionally explained in detail below.

The suction cap 300 is configured to surround the needles 100 and the central hub 200, and specifically, is engaged in close contact with the edge of one side of the central hub 200 and the inner circumference.

On the front of the suction cap 300 are formed needle penetrating holes 310 through which the needles 100 are passed, and a close contact hole 320 is formed adjacent to the needle penetrating holes 310. The needle penetrating holes 310 are sized so as not to interfere with the needles 100 which are moved in and out during procedure, and preferably, sized to almost correspond to the diameter of the needles 100. The needle penetrating holes 310 are configured in a manner of penetrating through the suction cap 300, and the close contact hole 320 is configured in fluid communication with the suction connecting hole 340 which will be explained below.

Figure 7:
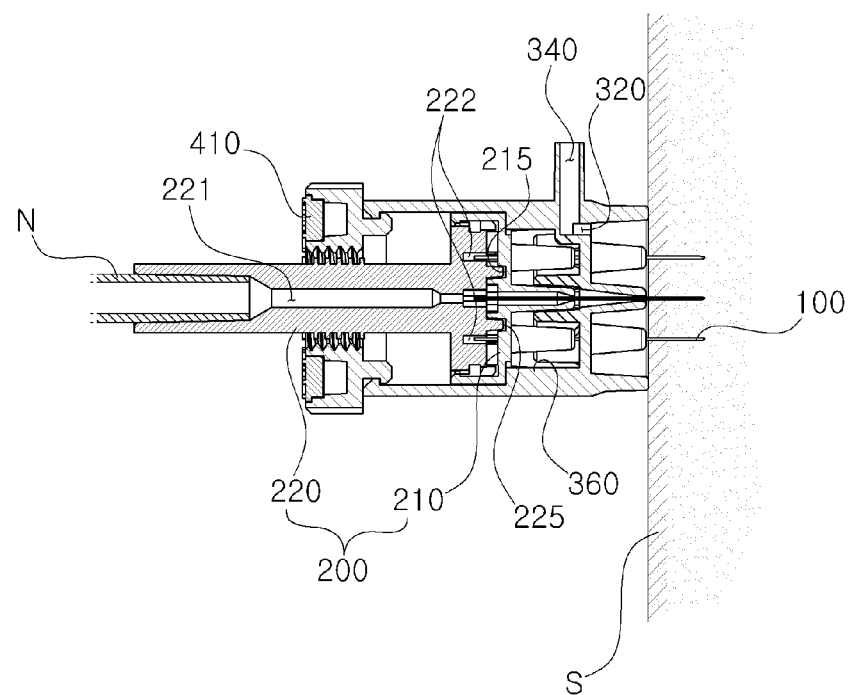

In the multineedle assembly 1 according to the present invention, the front surface of the suction cap 300 may be generally planar, but as illustrated in FIG. 1, may be configured into protrusion which is extended forward from a portion where the needle penetrating holes 310 are formed, and also is extended from the edge portion to a height that is same as, or slightly higher (preferably, about 0.2 mm higher, for efficient suction generation on the skin subject to procedure) than the protrusion where the needle penetrating holes 310 are formed. Additionally, the close contact hole 320 may preferably be formed on a relatively recessed portion on the protrusions where the needle penetrating holes 310 are formed. According to the present invention, the multineedle assembly 1 is connected to a suction device for generating a suction, so that in operation of the suction device, air is drawn in, causing completely tight contact between skin (S) and front end of the suction cap 300, as illustrated in FIG. 7. Accordingly, the multineedle assembly 1 is connected to the suction device to ensure that ends of the needle penetrating holes 310 are stably in tight contact with the skin (S) and continuous suction force is maintained at a location where the tight contact hole 320 is formed.

A space to accommodate front portion of the central hub 200 is formed at a rear portion of the needle penetrating holes 310, and a suction device connecting hole 340 is formed between this space and a space where the needle penetrating holes 310 are formed, in a fluid communication with the tight contact hole 320. The suction device connecting hole 340 is connected to the suction device to draw in air, so that by the operation of the suction device, the interior of the space formed by the front edge wall of the suction cap 300 has decreasing pressure, causing suction force to be generated.

The central hub 200 is movably connected so as to move forward and backward with reference to the suction cap 300, in which means such as guide protrusion 360 and guide hole 214 (to be explained below) allow the central hub 200 to move forward and backward with reference to the suction cap 300, while rotation of the suction cap 300 and the central hub 200 is prevented. Further, the central hub 200 is restricted between the suction cap 300 and the adjusting portion 400 so that it 200 is moved forward and backward in a limited range. Accordingly, when the central hub 200 is in the rear-most position within the forward and backward movable range, the needles 100 are not protruded forward the suction cap 300. Further, in this position, the front end of the suction cap 300 may preferably be aligned with the front end of the needles 100.

In the arrangement explained above, it is possible to easily adjust the length of exposure of the needles 100, as the needles 100 are not protruded forward the suction cap 300 and the degree of rotation of the adjusting portion 400 (to be explained below) corresponds to the length of exposure of the needles 100.

The adjusting portion 400 is rotatably connected to the rear end of the suction cap 300 in a screw engagement with the edge of one side of the central hub 200 to allow the central hub 200 to move forward and backward with reference to the suction cap 300 according to the direction of rotation, thereby adjusting the length of exposure of the needles 100. Part of entirety of the adjusting portion 400 has a larger diameter than the central hub 200, which allows a practitioner to easily grab the adjusting portion 400 and rotate the adjusting portion 400 with reference to the suction cap 300.

On one of the central hub 200 and the suction cap 300, a guide hole 214 is formed, while a guide protrusion 360 is formed on the other to be slidably guided along the guide hole 214.

As illustrated in FIG. 3, the guide hole 214 may be formed on the central hub 200, and as illustrated in FIG. 4, the guide protrusion 360 may be formed on the suction cap 300. A plurality of guide holes 214 and guide protrusions 360 may be formed along a circumferential direction, allowing the suction cap 300 to stably slide with reference to the central hub 200, while blocking the suction cap 300 from rotating circumferentially with reference to the central hub 200.

Figure 5:
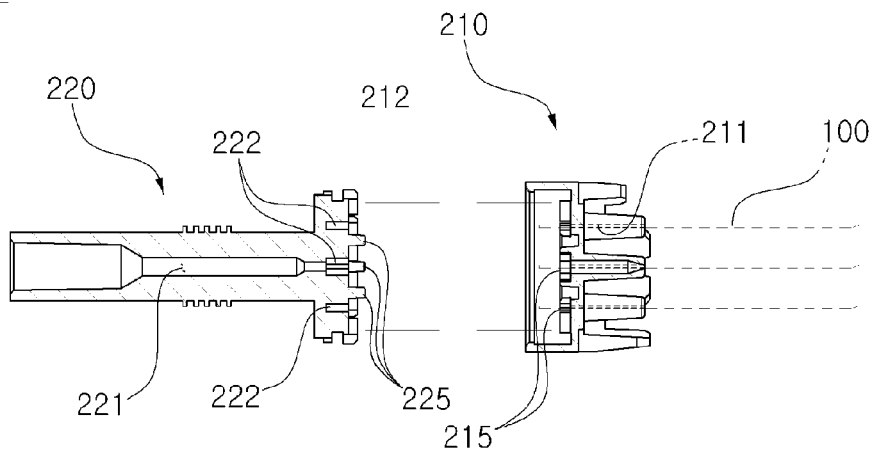
FIG. 5 is a cross section view of the central hub of FIG. 3.

FIG. 5 is a cross section view of the central hub 200 of FIG. 3.

The central hub 200 may be of an integrated type, in which the needles 100 are fixedly formed and connected to a syringe, but it is preferable that the central hub 200 may separately have a connecting portion 210 to which the needles 100 are fixedly connected, and an adjusting tubular portion 220 which forms a rear portion of the central hub 200 and connected with the adjusting portion 400 at an edge thereof.

The connecting portion 210 and the adjusting tubular portion 220 may be connected to each other, in which the front end of the adjusting tubular portion 220 is inserted into the rear end of the connecting portion 210 and locked therein. The adjusting tubular portion 220 may include an insert protrusion 225 formed on the front end, and the connecting portion 210 may have an insert hole 215 on the rear end to fittingly receive the insert protrusion 225 therein, which in turn prevents relative rotation of the connecting portion 210 and the adjusting tubular portion 220, and implement connection between the connecting portion 210 and the adjusting tubular portion 220 within a range that ensures fluid communication among second penetrating hole 221, second communicating hole 222, and needles 100.

The adjusting portion 400 is connected by being fitted in the adjusting tubular portion 220, and the adjusting portion 400 and the adjusting tubular portion 220 are screw engaged with each other. The screw engagement between the adjusting portion 400 and the adjusting tubular portion 220 may preferably be set to a degree that allows generation of sufficient friction that can allow fine adjustment of the adjusting portion 400, rather than loose fitting. The edge of the adjusting portion 400 may preferably have uneven configuration to prevent slipping and also to facilitate adjustment.

The adjusting portion 400 may have a series of numbers or scale along a circumference of the rear surface, which may be formed on a scale plate 410. The series of numbers may increase as the adjusting portion 400 is moved to the rear portion of the adjusting tubular portion 220. According to the direction or degree of rotating movement of the adjusting portion 400, the adjusting tubular portion 220 is moved along a lengthwise direction, i.e., forward and backward (in relative motion). Accordingly, because the degree of forward and backward movement of the adjusting tubular portion 220 corresponds distance of travel of the central hub 200 relative to the suction cap 300, i.e., to the length of exposure of the needles 100, the numbers or scale facilitate adjustment and determination of the length of exposure of the needles 100.

As a means to determine degree of length of exposure of the needles 100, the scale or the like may be formed on not only the adjusting portion 400, but also the adjusting tubular portion 220. Preferably, rather than being configured into a complete cylinder form, the adjusting tubular portion 220 may have partial plane which is formed by cutting away a portion thereof, on which the scale or the like may be formed, as explained in FIG. 2. The portion of the adjusting tubular portion 220 where the scale or the like is formed, serves as the scale portion 223.

When the portion of the adjusting tubular portion 220 having screw thread has such an outer circumference that causes complete fitting with the inner diameter of the adjusting portion 400, subsequently-increased friction would allow fine adjustment of the adjusting portion 400. However, greater friction than required can interfere with the maneuvering of the adjusting portion 400. The present invention takes the above into consideration, so that the adjusting tubular portion 220 is partially formed as a cylinder, but with a portion cutaway to form a plane on which the scale portion 223 is formed, thus causing proper degree of friction between the adjusting portion 400 and the adjusting tubular portion 220 and allowing easy maneuver.

Further, by marking numbers or scale in a lengthwise direction on the scale portion 223, it is further facilitated to check the length of exposure of the needles 100.

Meanwhile, it is preferable that the scale or the like may be formed on a separate scale plate 410 to be connected to the adjusting portion 400 for reasons explained below, although the scale or the like may be directly formed on the adjusting portion 400.

The screw thread is formed on the inner circumference of the adjusting portion 400 and screw engaged with the adjusting tubular portion 220. While the adjusting portion 400 has to be set to zero when the adjusting tubular portion 220 of the central hub 200 is at the rear-most position with reference to the suction cap 300, it is not easy to set to zero, considering position, size, or the like of the screw thread formed on the adjusting portion 400 and the adjusting tubular portion 220.

Accordingly, with the adjusting portion 400 fit in the adjusting tubular portion 220 and with the adjusting tubular portion 220 being placed at the rear-most position with reference to the suction cap 300, it is possible to accurately adjust to zero by fitting the scale plate 410 to the adjusting portion 400 and adjusting to zero. At the same time, the front end of the needles 100 are aligned with the front end of the need penetrating holes 310.

The connecting portion 210 includes first penetrating holes 211 through which the needles 100 are respectively passed through, and first communication holes 212 respectively formed on rear ends of the first penetrating holes 211. The first penetrating holes 211 may be sized to have such a diameter that is fit for the needles 100, or some areas may be sized to have larger diameters than the needles 100.

In the former's case, the first communicating holes 210 may respectively have larger diameters than the first penetrating holes 211, and the plurality of first communicating holes 210 are configured in fluid communication with each other.

In the latter's case, the first penetrating holes 211 may be configured in a tapered manner so that these 211 generally fit for the diameter of the needles 100 in the front direction, while having gradually increasing diameter backward. Alternatively, the first penetrating holes 211 may be configured in a manner so that these 211 generally fit for the diameter of the needles 100 in the front and rear directions, while having larger diameter than the needles 100 in the middle.

The adjusting tubular portion 220 includes second penetrating holes 221 in fluid communication with the nozzle (N) of the syringe, and second communicating holes 222 formed on front ends of the second penetrating holes 221.

Further, the second communicating holes 222 are in fluid communication with the all of the first communicating holes 212.

As explained above, in the configuration of the central hub 200 according to the present invention, the connecting portion 210 and the adjusting tubular portion 220 are separately formed and connected to each other, thereby facilitating fixing the needles 100, distribution of the fluid delivered from the nozzle (N) of the syringe to the respective needles 100, which will be explained in detail below.

It is necessary that the multineedle assembly 1 according to the present invention is configured so that the fluid discharged through one single exit such as syringe nozzle (N) is evenly distributed and moved to the respective needles 100, but this structural characteristic requires rather complex structure inside the central hub 200 (due to first penetrating holes 211 and portions connecting thereto).

Because the connecting portion 210 has the first penetrating holes 211 and the first communicating holes 212 therein, if the first penetrating holes 211 are larger than the diameter of the needles 100, it is possible to fill the interior of the first penetrating holes 211 with adhesive which may be introduced through the first communicating holes 212. Accordingly, the needles 100 can be firmly connected to the connecting portion 210, respectively.

If the first penetrating holes 211 are configured to fit the needles 100, because the first communicating holes 212 have larger diameter than the first penetrating holes 211, again, it is possible to firmly connect the needles 100 to the connecting portion 210 by filling in the first communicating holes 212 with adhesive, or the like. The rear ends of the needles 100 is inserted into the second communicating holes in fluid communication therewith.

The adjusting tubular portion 220 includes the second communicating holes 222 formed on the front end, which are in fluid communication with all of the first communicating holes, and eventually, with all of the needles 100. Accordingly, when the adjusting tubular portion 220 is connected to the rear end of the connecting portion 210, the fluid discharged from the syringe nozzle (N) is evenly distributed and moved to the needles 100, respectively.

Figure 6:
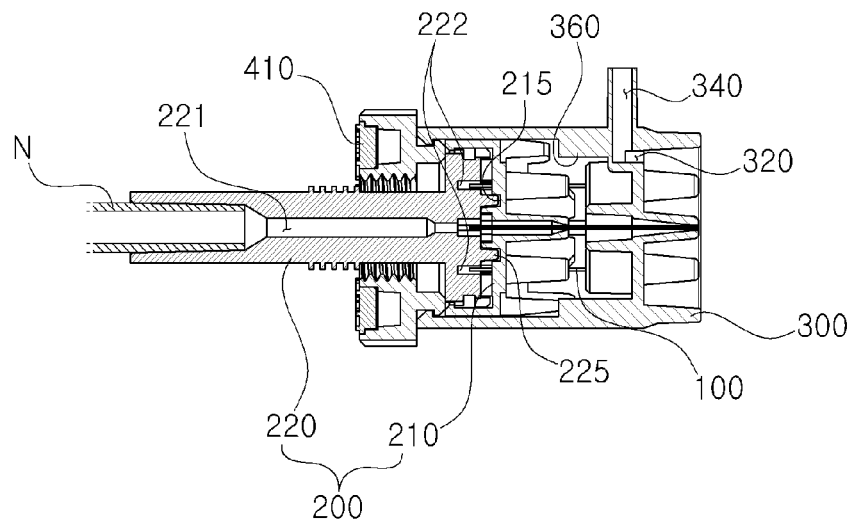
FIGS. 6 and 7 illustrate the process of operating the multineedle assembly of FIG. 1 in cross section view.

FIGS. 6 and 7 illustrate the process of operating the multineedle assembly of FIG. 1 in cross section view.

The process of operating the multineedle assembly 1 according to the present invention will be briefly explained.

The adjusting portion 400 is rotated to thus adjust the length of exposure, according to the length to which the needles 100 of the multineedle assembly 1 are required to be exposed.

With the needles 100 being in non-exposed position on the front end of the suction cap 300, by rotating the adjusting portion 400 with reference to the suction cap 300, the central hub 200 is moved forward with reference to the suction cap 300, causing the needles 100 to protrude out of the needle penetrating holes 310. Because the length of the exposure of the needles 100 is readily checked based on the scale plate 410 of the adjusting portion 410 and/or numbers marked on the scale portion 223 of the adjusting tubular portion 220, a practitioner can adjust the length of exposure to that is desired, and confirm the correct adjustment, without having to use a separate tool.

Further, referring to FIG. 6, the syringe nozzle (N) is connected to the rear end of the multineedle assembly 1, i.e., to the rear end of the adjusting tubular portion 220.

Additionally, the suction device is connected to the suction device connecting hole 340. After that, a practitioner places the front end of the suction cap 300 to close contact with the skin (S) of the patient and is prepared for the procedure.

Once the needles 100 are inserted into the skin, operation of the suction device causes the pressure to decrease inside the front portion formed by the edge wall of the front end of the suction cap 300. Accordingly, the skin (S) of the patient is pressed to tight contact toward the close contact hole 320, and also to the end of the needle penetrating holes 310.

Referring to FIG. 7, with the needles 100 being in completely inserted state in the skin (S), fluid is injected through the syringe nozzle (N) and the procedure is completed.

Figure 8:
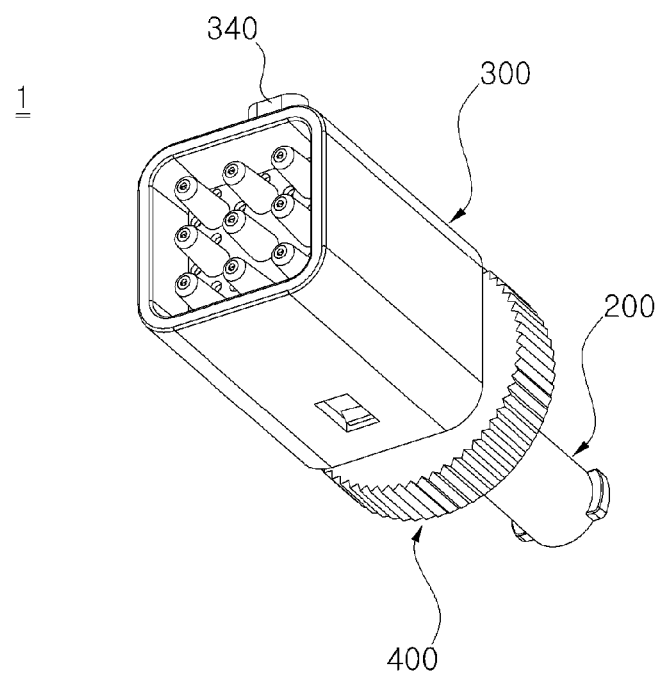
FIGS. 8 and 9 are perspective views of the multineedle assembly according to another embodiment of the present invention.
Figure 9:
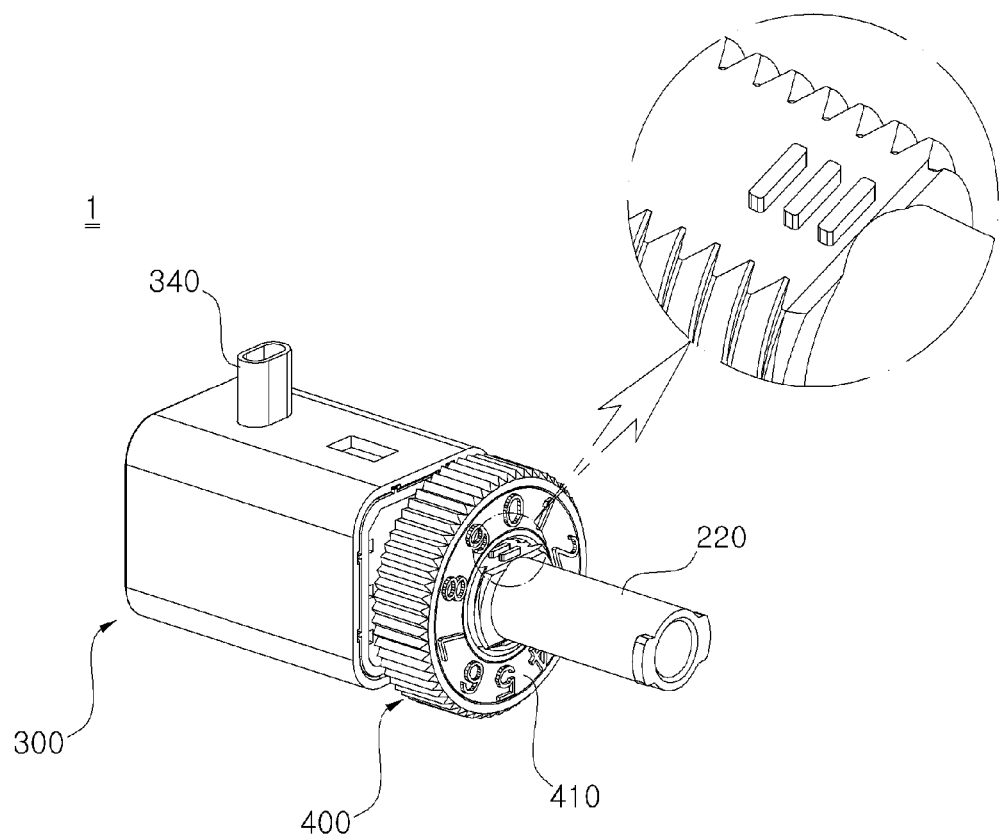

FIGS. 8 and 9 are perspective views of the multineedle assembly according to another embodiment of the present invention.

The central hub 200, or more particularly, the connecting portion 210 may have approximately rectangular cross section, and the suction cap 300 may also have approximately rectangular cross section. Because the central hub 200 is moved forward and backward with reference to the suction cap 300, rectangular cross section can ensure stable operation because it can prevent rotation of the central hub 200 to the rotating direction of the adjusting portion 400 with reference to the suction cap 300. In another embodiments, the connecting portion 210 and the suction cap 300 may have polygonal cross section rather than rectangular cross section.

INDUSTRIAL APPLICABILITY

The multineedle assembly according to the present invention is accurately adjustable in the depth it is penetrated into skin by a simple manipulation, allows checking on the adjustment, and provides stable operation, and therefore, applicable to treatment of a variety of skin troubles, hair loss and obesity.

What is claimed is:
1. A multineedle assembly, comprising:
 a plurality of needles;
 a central hub exposing front portions of the needles, while surrounding rear portions of the needles to fix the needles in place;
 a suction cap surrounding one side of the needles and the central hub, being in close contact with the central hub, and comprising needle penetrating holes through which the needles are passed; and
 an adjusting portion rotatably connected to a rear end of the suction cap, being screw engaged with an edge of one side of the central hub to move the central hub with respect to the suction cap according to a direction of rotation, to thereby adjust a length that the needles are exposed, the adjusting portion having a series of numbers of scale on one side along the direction of rotation.
2. The multineedle assembly of claim 1, wherein the suction cap comprises a close contact hole on a front portion which is separated from the needle penetrating holes, and a suction device connecting hole on one side which is in fluid communication with the close contact hole.

3. The multineedle assembly of claim 1, wherein the needles are not protruded forward the suction cap, when the central hub is in a rear-most position with respect to the suction cap.

4. The multineedle assembly of claim 1, wherein either one of an outer side of the central hub and an inner side of the suction cap comprises a guide groove, while the other one of the inner side of the suction cap and the outer side of the central hub that does not have the guide groove comprises a guide protrusion to be slid along the guide groove.

5. The multineedle assembly of claim 1, wherein an adjusting tubular portion is provided, which forms a rear portion of the central hub and which is connected to the adjusting portion, and the adjusting portion is configured to surround the adjusting tubular portion.

6. The multineedle assembly of claim 1, wherein the adjusting portion is in close contact with a rear end of the suction cap, and has a larger diameter than the suction cap.

7. A multineedle assembly of claim 1, wherein the central hub comprises a connecting portion to which the needles are fixedly connected, an adjusting tubular portion whose rear end is connected to a syringe nozzle and an edge is connected to the adjusting portion, wherein the connecting portion comprises first penetrating holes through which the respective needles are passed, first communicating holes formed on rear ends of the first penetrating holes with increasing diameter, and wherein the adjusting tubular portion comprises second penetrating holes in fluid communication with the syringe nozzle, second communicating holes formed on front ends of the second penetrating holes, wherein the second communicating holes are in fluid communication with all of the needles.

8. The multineedle assembly of claim 7, wherein two or more insert protrusions are formed on either one of a rear end of the connecting portion and a front end of the adjusting tubular portion, while insert holes to fittingly receive the insert protrusions therein are formed on the other one which do not have the insert protrusions.

9. The multineedle assembly of claim 7, wherein at least part of the first penetrating holes have larger diameter than that of the needles, and the needles are fixed as adhesive is filled in the first penetrating holes.

10. The multineedle assembly of claim 1, wherein the central hub and the suction cap have a polygonal cross section.

* * * * *